US006854332B2

(12) United States Patent
Alleyne (10) Patent No.: US 6,854,332 B2
(45) Date of Patent: Feb. 15, 2005

(54) INSPECTION OF NON AXI-SYMMETRIC ELONGATE BODIES

(75) Inventor: David N. Alleyne, Middlesex (GB)

(73) Assignee: Guided Ultrasonics (Rail) Ltd., Nottingham (GB)

( * ) Notice: Subject to any disclaimer, the term of this patent is extended or adjusted under 35 U.S.C. 154(b) by 0 days.

(21) Appl. No.: 10/470,347

(22) PCT Filed: Nov. 28, 2001

(86) PCT No.: PCT/GB01/05262

§ 371 (c)(1),
(2), (4) Date: Dec. 2, 2003

(87) PCT Pub. No.: WO02/059593

PCT Pub. Date: Aug. 1, 2002

(65) Prior Publication Data

US 2004/0093949 A1 May 20, 2004

(30) Foreign Application Priority Data

Jan. 26, 2001 (GB) .............................................. 0102118

(51) Int. Cl.⁷ .............................................. G01N 29/04
(52) U.S. Cl. ........................................ 73/636; 73/633
(58) Field of Search .......................... 73/636, 632–635, 73/643, 544, 577–578

(56) References Cited

U.S. PATENT DOCUMENTS 3,978,712 A 9/1976 Cowan et al.
4,646,572 A 3/1987 Boettger et al.
5,419,196 A 5/1995 Havira et al.
6,424,150 B2 * 7/2002 Kwun et al. ................. 324/216
6,516,668 B2 * 2/2003 Havira et al. ................. 73/636

FOREIGN PATENT DOCUMENTS

| DE | 32 18 453 A | 11/1983 |
| EP | 0159933 A1 | 10/1985 |
| WO | 94/20847 A1 | 9/1994 |
| WO | WO 96/12951 | 5/1996 |
| WO | 99/66320 A1 | 12/1999 |

OTHER PUBLICATIONS

L. Gavric, "Computation of Propagative Waves in Free Rail Using a Finite Element Technique" *Journal of Sound and Vibration*, vol. 185, pp 531–543, 1995.

* cited by examiner

*Primary Examiner*—Helen Kwok
(74) *Attorney, Agent, or Firm*—Nixon & Vanderhye, P.C.

(57) ABSTRACT

Apparatus for inspecting a non axi-symmetric elongate body includes at least one exciter array having a plurality of wave exciters that can be coupled to an exterior surface of the elongate body. A driver unit generates driving signals to excite the wave exciters. Each driving signal for a respective wave exciter in the array is weighted with respect to driving signals to the other wave exciters in the array such that a specific guided acoustic wave mode is excited. A receiving unit includes a plurality of wave receivers for receiving reflected guided acoustic waves. An analysis unit analyzes received waves to assess a condition of the non axi-symmetric elongate body.

18 Claims, 7 Drawing Sheets

INSPECTION OF NON AXI-SYMMETRIC ELONGATE BODIES

This application is the US national phase of international application PCT/GB01/05262 filed 28 Nov. 2001, which designated the US.

TECHNICAL FIELD

The present invention relates generally to the inspection of non axi-symmetric elongate bodies, such as, for example, the rails of a railway track for cracks, fatigue, weaknesses in welds or any other structural deformation.

Regular inspection of the condition of rails is imperative to ensure the safety of a rail network. The large distances of rail involved and the need to avoid interruptions to train services make inspection of rails difficult to implement. Known techniques for the inspection of rails include ultrasonic inspection. A wave exciting element such as a transducer is placed on a specific section of rail and is used to induce bulk waves that can be longitudinal or shear to travel through the rail. These bulk waves are be used to inspect the portion of rail immediately adjacent to the transducer location. This technique has the disadvantage that only small lengths of rail can be tested at a time and the section of rail being tested is out of use by trains during the test process. The inspection may be carried out by sliding one or more ultrasonic transducers along the rail by mounting them on a cart or on a special inspection train.

Figure 1:
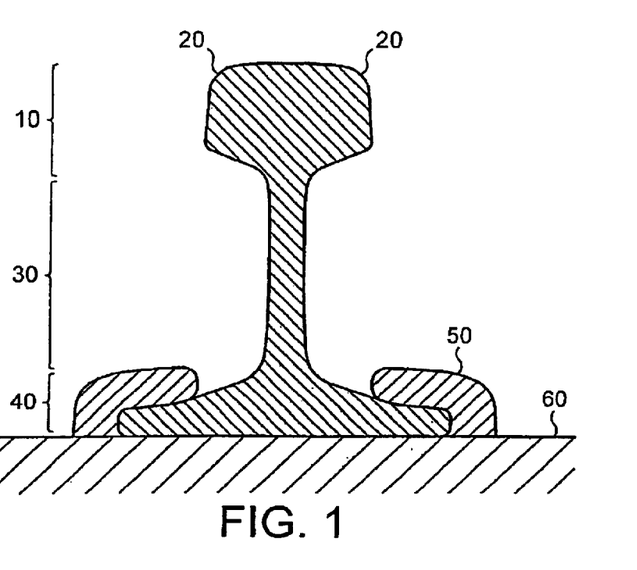
FIG. 1 is a schematic diagram of a transverse cross section of a rail.

FIG. 1 illustrates schematically a cross-section of a railway rail. The rail comprises a head 10 with curved upper corners 20; a stem-like web 30 extending from the head down to a broad toe section 40 that supports the head and web. The rail is secured onto a sleeper 60 by a clip 50 on either side of the toe 40. The rail has a vertical plane of symmetry through the centre of the web 30, but is non axi-symmetric.

The geometry of the rail makes it difficult to inspect all regions of the structure and, in particular, conventional ultrasonic techniques make it difficult to inspect the toe region 40 because the clips 50 restrict the access of transducers in this area. The sides of the head region are also difficult to inspect due to the curvature of the corners 20 which means that the transducers will be unlikely to sit flush on this region of the head. Inspection of the "thermit" welds that join adjacent sections of rail is difficult using the standard ultrasonic test equipment because these welds are castings which attenuate strongly at the ultrasound frequencies typically used, such as 1 to 5 MHz.

It is known from International Patent Application WO-A-96/12951 to use guided acoustic waves that propagate along pipes to test those pipes for defects. The axi-symmetric nature of the pipes allow control over the particular guided wave modes excited by applying axi-symmetric excitation, thereby dealing with the complication of the large number of closely related possible guided wave modes. This solution does not work in non axi-symmetric systems.

The invention provides an apparatus for inspecting a non axi-symmetric elongate body comprising:

at least one exciter array having a plurality of wave exciters operable to couple to an exterior surface of said elongate body;

a driver unit operable to generate driving signals to excite said plurality of wave exciters wherein each driving signal to a respective wave exciter of said array is weighted with respect to driving signals to other wave exciters in said array such that at least one guided acoustic wave mode is excited;

a receiving unit having a plurality of wave receivers capable of receiving reflected guided acoustic waves; and an analysis unit operable to analyze received waves to assess a condition of said non axi-symmetric elongate body.

The invention provides a technique whereby guided wave inspection may be employed for non axi-symmetric elongate bodies by using appropriate weighted driving signals to a plurality of wave exciters coupled to the surface of the elongate body. Analysis of the guided wave modes of the elongate body performed in advance yields information regarding the relative displacements at different points on the surface of the body for different modes. By adopting appropriate weightings matched to these calculated mode specific displacements, a selected guided wave mode can be excited and used to inspect the elongate body.

In order to improve performance by helping suppress unwanted guided wave modes and/or suppressing propagation in a reverse direction, preferred embodiments of the invention employ a plurality of arrays of wave exciters to give additional control over the mode excited.

It will be appreciated that separate exciters and receivers could be provided. However, an advantageous gain in efficiency and simplicity is achieved when the exciter array is operated in a pulse-echoing mode whereby the exciters also serve as receivers.

The ability to analyse reflected signals is improved by the use of a technique whereby the signals from each receiver are multiplied by a respective weighting factor appropriate to a particular reflected guided wave mode to determine the strength of signal in that reflected guided wave mode.

Whilst information regarding defects or the general condition of the elongate body can be recovered from a wide variety of guided modes, preferably the excited mode is a symmetric mode with respect to the elongate body and the particular received wave mode is either a predetermined non-symmetric or the mode corresponding to the excited mode. It is preferred to analyse both received symmetric and received non-symmetric modes.

The non axi-symmetric nature of the elongate body whilst it introduces a difficulty compared to axi-symmetric pipes, does allow for the possibility of particular excited guided wave modes to concentrate on particular areas of the non axi-symmetric elongate body to reveal more information regarding those particular areas. As an example, different excited guided wave modes can be used to concentrate upon the head, web and toe of a railway rail.

Whilst the exciters could be fixed to the elongate body in a variety of different ways, in a preferred embodiment the exciter array is secured to the elongate body by a clamping mechanism. Such a clamping mechanism may be either temporarily or permanently fixed to the elongate body. In a further preferred embodiment the transducers are bonded to the rail.

It is particularly convenient to form the exciters using piezoelectric transducers.

Whilst the technique of the present invention could be used to examine a wide variety of different non axi-symmetric elongate bodies, such as structural members within bridges or buildings, the invention has particular utility in the testing of railway rails.

Whilst the exciters may be simultaneously driven, preferred embodiments sequentially drive different exciters. In this case synthetic aperture processing techniques (synthesised transmission and synthesised reception respectively) may be used to analyse the received waves.

Viewed from another aspect the present invention provides a method of inspecting a non-axi-symmetric elongate body comprising the steps of:

driving a plurality of wave exciters coupled to said elongate body with driver signals, each driver signal to a respective wave exciter being weighted with respect to driving signals to other wave exciters such that at least one guided acoustic wave mode is excited;

receiving reflected guided acoustic waves; and analysing said received waves to assess a condition of said elongate body.

BRIEF DESCRIPTION OF THE DRAWINGS

Embodiments of the apparatus for inspecting non axi-symmetric elongate bodies will now be described, by way of example only, with reference to the accompanying figures, in which.

DETAILED DESCRIPTION

The guided wave modes that can propagate in a rail at a given frequency are identified using a technique similar to that described by L. Gavric 'Computation of propagative waves in free rail using a finite element technique', Journal of Sound and Vibration, Vol 185, pp 531–543. This is based on the finite element method, but only a cross section of the rail is modelled.

Figure 2:
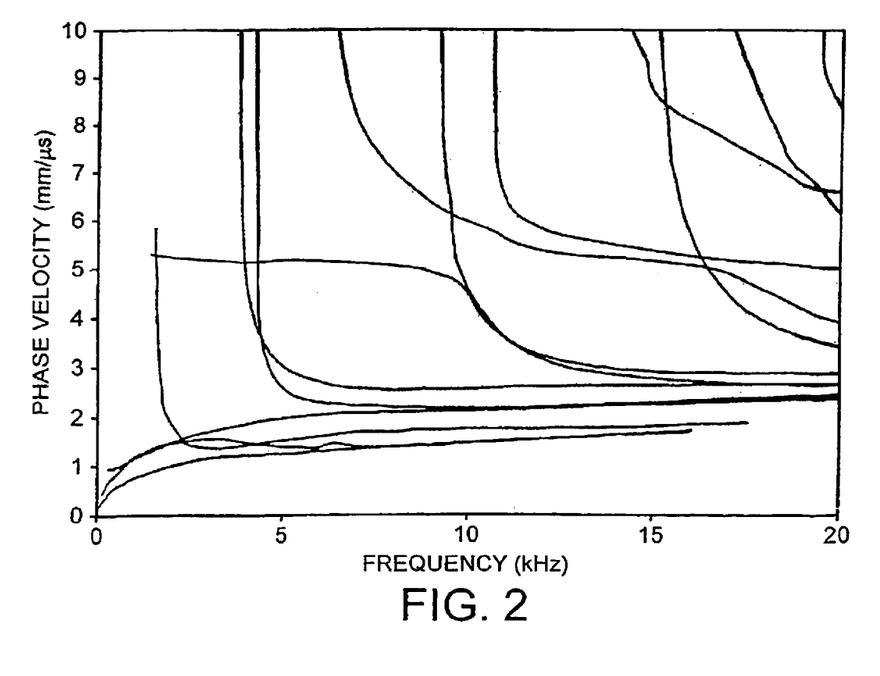
FIG. 2 illustrates the dispersion curves of a rail.

FIG. 2 shows phase velocity dispersion curves for a rail that were obtained using the technique referred to above. These dispersion curves can be used to identify the guided wave modes that will propagate in the rail at a given frequency. It can be seen from FIG. 2 that the different modes present at a given frequency typically have different propagation velocities. FIGS. 3 to 6 are examples of mode shapes for the rail corresponding to guided waves propagating at a frequency of about 17 kHz. These mode shapes are calculated using a method similar to that of Gavric. These mode shapes are a representative sample and are not the only mode shapes propagating at the specified frequency. Each of FIGS. 3 to 6 shows a two dimensional finite element mesh model of the rail. The x axis runs vertically and parallel to the web of the rail; the y axis runs horizontally and parallel to the toe; and the z axis runs parallel to the length of the rail. In each case the deformed web corresponding to the particular propagation mode is plotted alongside the undeformed mesh in which no waves have been excited.

Figure 3:
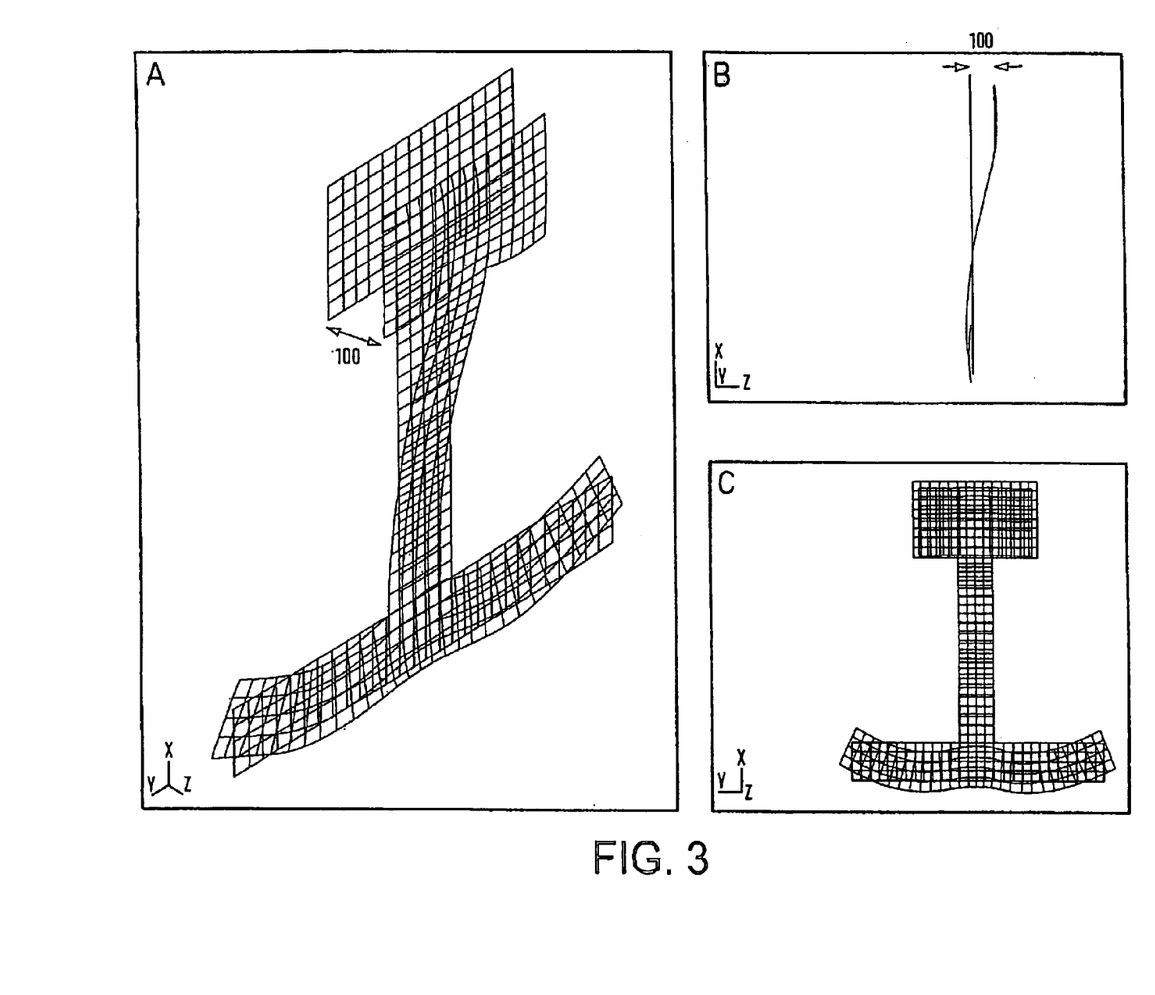
FIG. 3 illustrates a symmetric mode of a propagating guided wave in which the motion of the head section of the rail is dominant.

FIG. 3 shows the rail displacements for a mode in which the head motion is dominant. FIG. 3A shows a view of the mesh looking directly between the y and the z axes. The displacement 100 of the head along the z-axis is characteristic of this mode. The upper portion of the web also undergoes some displacement along the z-axis in the same direction as the head. FIG. 3B is a view along the y-axis that illustrates the displacement with respect to the vertical. The lower portion of the web is displaced by a small amount from the vertical in the opposite direction with respect to the head. FIG. 3C is a view along the z-axis and this shows that there is some displacement of the web which deforms upwards in the middle and at either extremity. FIG. 3C also illustrates that this head-mode is symmetric with respect to an axis of symmetry running through the centre of the web and parallel to the x-axis.

Figure 4:
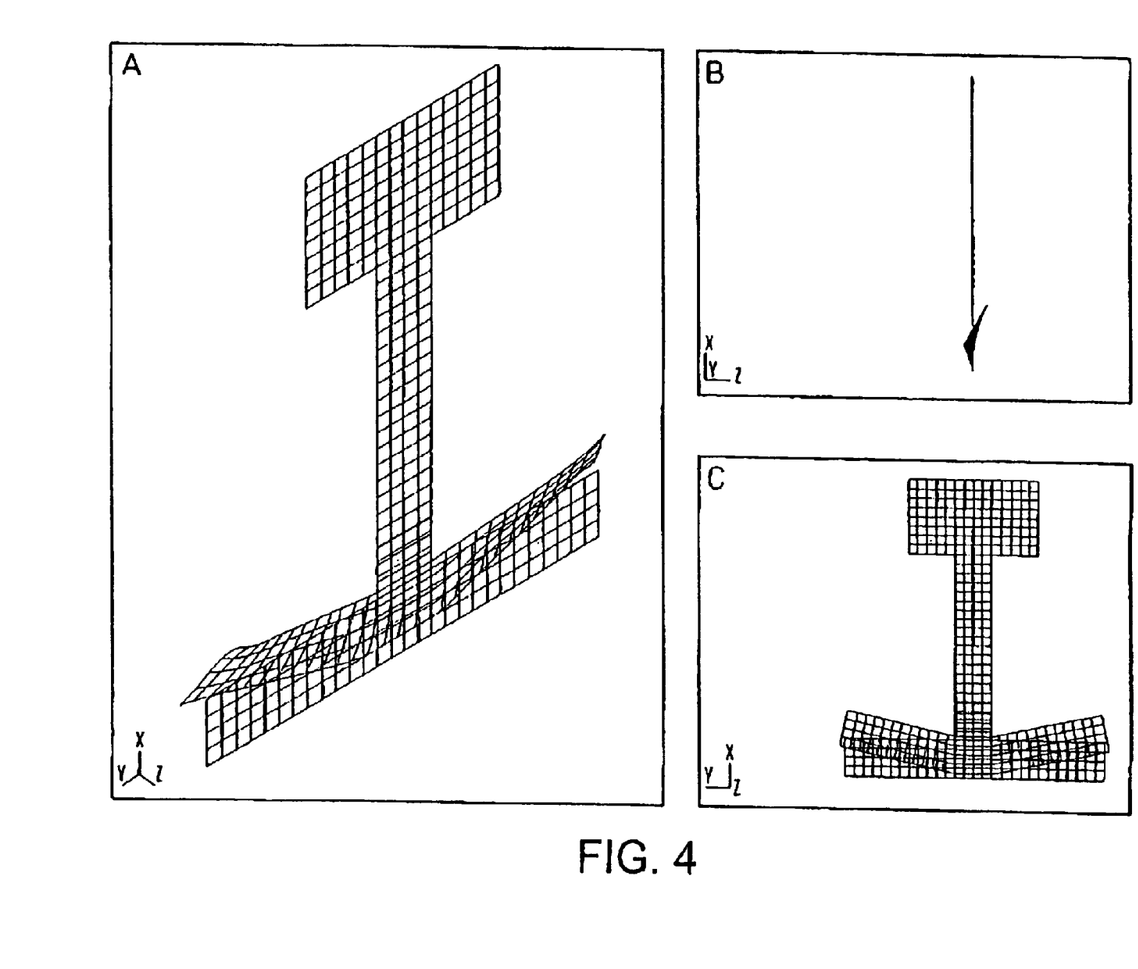
FIG. 4 illustrates a symmetric mode of a propagating guided wave in which the motion of the toe section of the rail is dominant.

FIG. 4 shows the rail displacements for a mode in which the toe motion is dominant. FIG. 4A shows a view of the mesh looking directly between the y and the z axes. The displacement of the toe is characteristic of this mode. The extremities of the toe along the y-axis both undergo displacements in the positive x direction. The displacements are almost completely confined to the toe region. FIG. 4B is a view along the y axis that illustrates the displacement of the extremities of the toe with respect to the vertical. Opposite extremities of the toe are displaced in opposite directions along the z axis such that the rectangular strip corresponding to the undisplaced toe is twisted. FIG. 4C is a view along the z axis and this shows more clearly the upwards x displacement that increases gradually towards the extremities of the toe. FIG. 4C also illustrates that this toe-mode is symmetric with respect to an axis of symmetry running through the centre of the web and parallel to the x axis.

Figure 5:
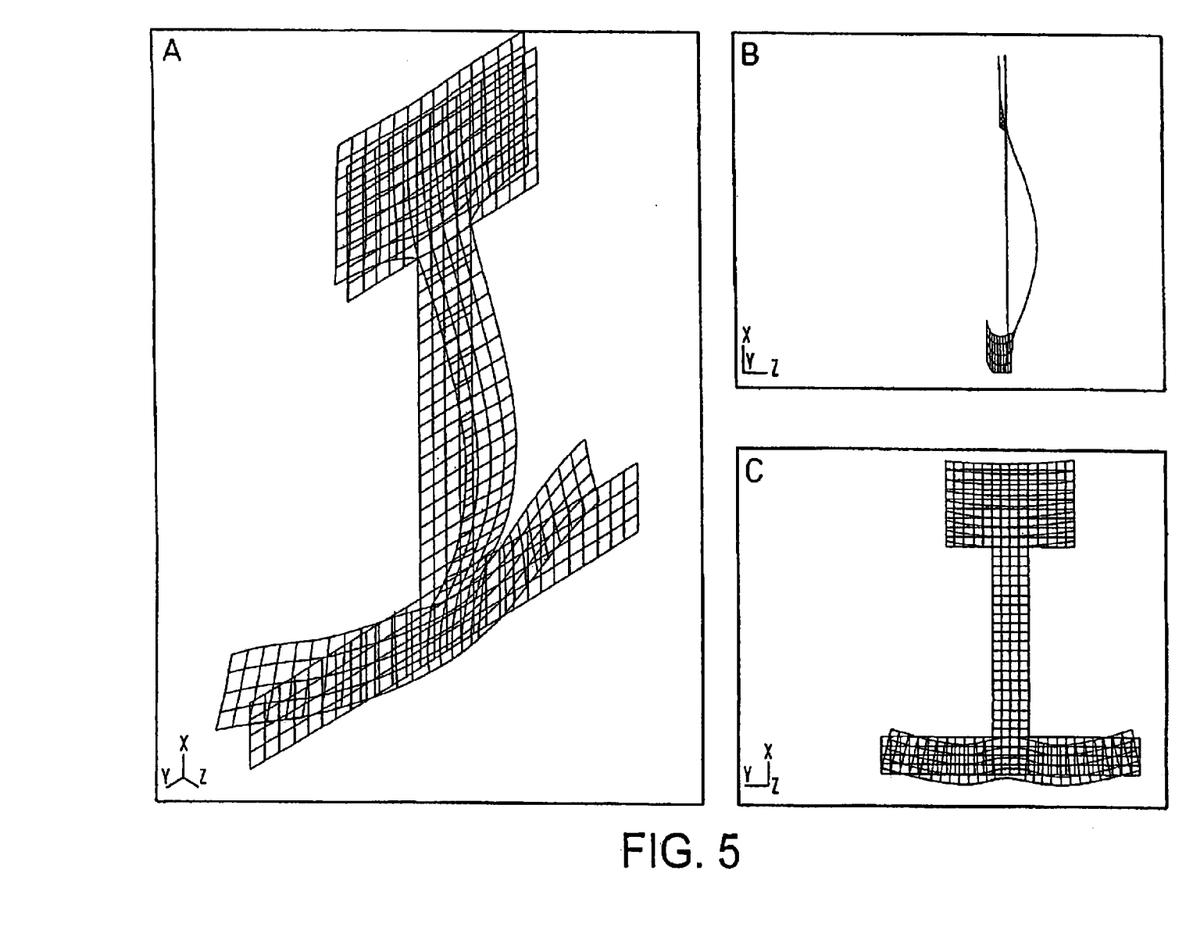
FIG. 5 illustrates a symmetric mode of a propagating guided wave in which the motion of the web section of the rail is dominant.

FIG. 5 shows the rail displacements for a mode in which the web motion is dominant. FIG. 5A shows a view of the mesh looking directly between the y and the z axes. The large displacement of the web along the z-axis is characteristic of this mode. The toe also experiences some displacement in this mode. FIG. 5B is a view along the y axis that illustrates the large displacement of the extremities web with respect to the x-axis. The displacement has a maximum at the centre of the web and this decreases gradually towards the extremities of the web. The head is displaced by a small amount in a direction opposite to the displacement of the web. FIG. 5C is a view along the z axis and this shows more clearly the displacement of the toe. FIG. 5C also illustrates that this web-mode is symmetric with respect to an axis of symmetry running through the centre of the web and parallel to the x axis.

Figure 6:
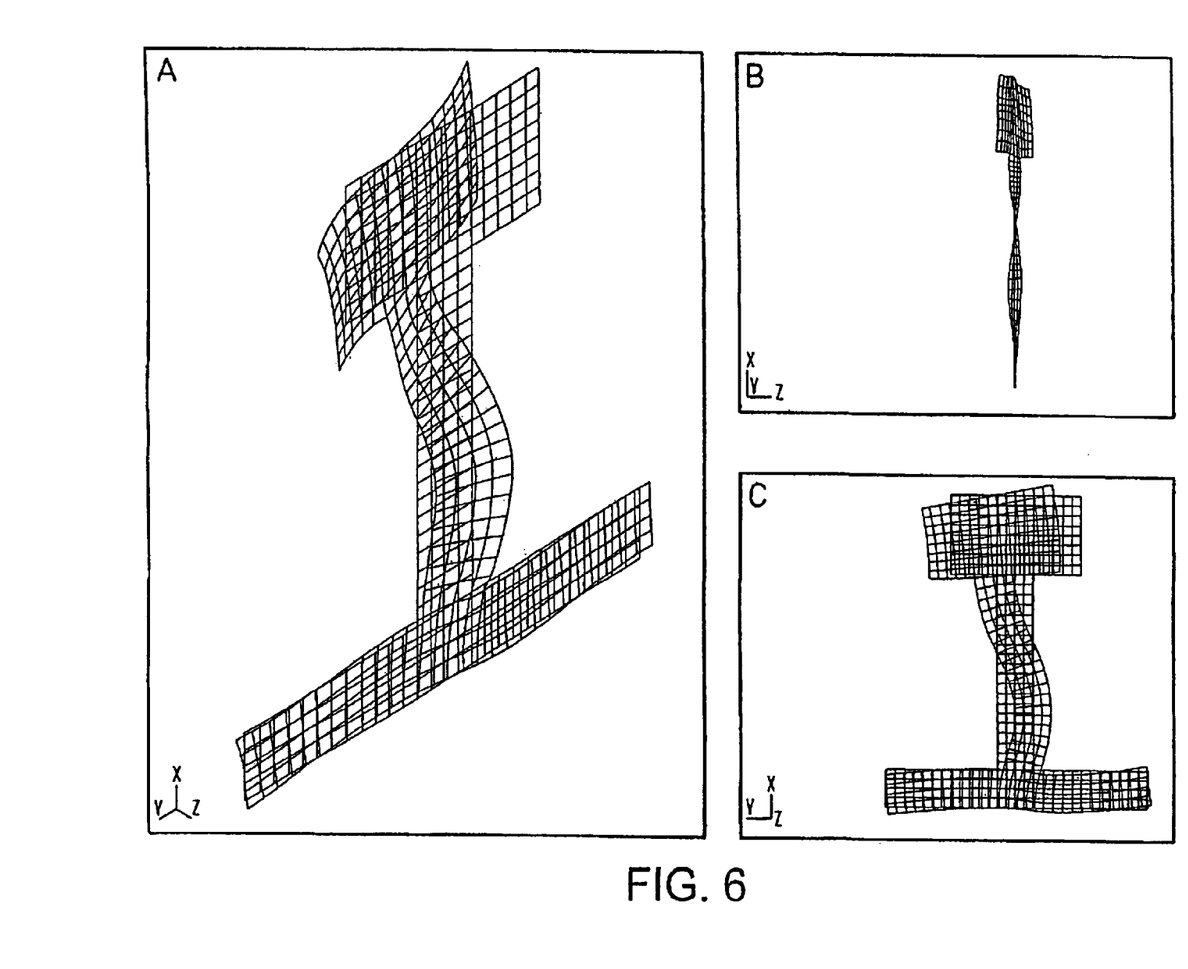
FIG. 6 illustrates an anti-symmetric mode of a propagating guided wave in which the motion of both the head section and the web section of the rail are dominant.

FIG. 6 shows the rail displacements for a mode that is anti-symmetric with respect to an axis of symmetry running through the centre of the web and parallel to the x axis. FIG. 6A shows a view of the mesh looking directly between the y and the z axes. The web is subject to considerable curvature in the x-y plane and the head undergoes displacement in the z direction such that opposite extremities of the head along the y-axis are displaced in opposite directions along the z-axis. FIG. 6B is a view along the y-axis that illustrates the twisting of the web along the x-axis. FIG. 6C is a view along the z-axis and this shows more clearly the dominant displacements of the head and web together with small displacements in the toe.

The modes that can be excited are either symmetric or anti-symmetric with respect to the plane of symmetry of the rail that runs vertically through the centre of the web along the length of the rail. If a symmetric wave such as that of FIG. 3 is incident on a feature such as a weld that is also symmetric with respect to the plane of symmetry then it is unlikely that any modes excited in the rail will mode-convert to anti-symmetric modes such as the mode illustrated in FIG. 6. However defects in the rail such as cracks are highly unlikely to be symmetric, so when a symmetric mode reflects at a crack it will typically be at least partially mode-converted to an anti-symmetric mode having the same frequency as the symmetric outgoing wave. In this case, the reflected signal will include both symmetric and anti-symmetric modes. Analysing the properties of the reflected waves provides a way of distinguishing between the presence of structural defects that induce mode-conversion from good welds that are typically substantially symmetric therefore they do not induce mode conversion. In this embodiment only symmetric modes are excited by the wave exciter array. Alternatively only anti-symmetric modes could be excited that would only mode convert to symmetric modes at a non-symmetric feature. Regardless of whether the excited mode is symmetric or anti-symmetric, the receivers should be capable of detecting both symmetric and non-symmetric modes in the reflected waves. If the defect from which an excited mode reflects is symmetric then only the mode-type of the excited wave will typically be received. Thus, the absence of the anti-symmetric mode-converted wave indicates that the reflector is likely to be symmetric.

Figure 7:
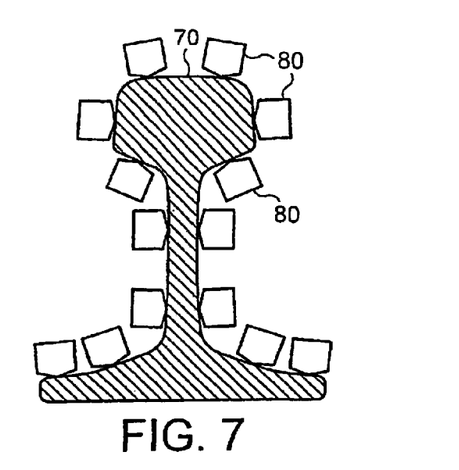
FIG. 7 schematically illustrates a typical transducer array according to a first embodiment of the invention.

FIG. 7 shows a cross-section of a rail 70 with an array of transducers 80 according to a first embodiment of the invention deployed at fourteen positions on the surface of the rail. In this embodiment a total of fourteen transducers are arranged around a single cross section of the rail such that six are disposed on the head, four are disposed on the web and four are disposed on the toe of the rail. The number of transducers required increases with the number of unwanted modes to be suppressed and with the complexity of the mode shapes to be excited. The transducers could be bonded to the rail, although alternative clamping arrangements are described later.

In an alternative embodiment the transducers arranged in a linear array along the length of the rail.

Each transducer is formed from a piezoelectric element (electro-magnetic acoustic transducers (EMATS) may also be used and may be preferred in embodiments in which the transducers are mounted on a moving train rather than being clamped to the rail) that is polarised to deform when a voltage is applied across its faces. Thus, each transducer can act as a wave exciter. The voltage applied to each transducer can be adjusted independently according to the amount of deformation required at the corresponding point on the rail surface. Each transducer can also act as a wave receiver by converting the deformations due to the propagation of waves along the rail to electrical signals. The transducer array is provided with a driving mechanism that is capable of supplying a different driving voltage to each transducer. The driving mechanism consists of a multi-channel signal generator and a power amplifier capable of adjusting each output channel independently. The output from the power amplifier is used to supply excitation signals to high impedance piezoelectric transducers that serve as wave exciters. The input voltage to each transducer in the array is weighted with respect to the other transducers of the array such that the overall pattern of excitation corresponds to the desired mode shape. The weightings required to excite a particular mode are calculated using a method similar to that of Gavric as previously discussed.

EMATs may also, be permanently attached to the rail at strategic points to detect defects at welds.

The transducer array can be used to excite several modes in turn. This can be used to specifically target defects occurring in the particular parts of the rail preferentially displaced by a given mode. For example the mode shown in FIG. 3 is largely confined to the head, the mode shown in FIG. 4 is largely confined to the toe and the mode shown in FIG. 5 is largely confined to the web hence these modes can be used to identify defects in the head, toe and web of the rail respectively.

Figure 8:
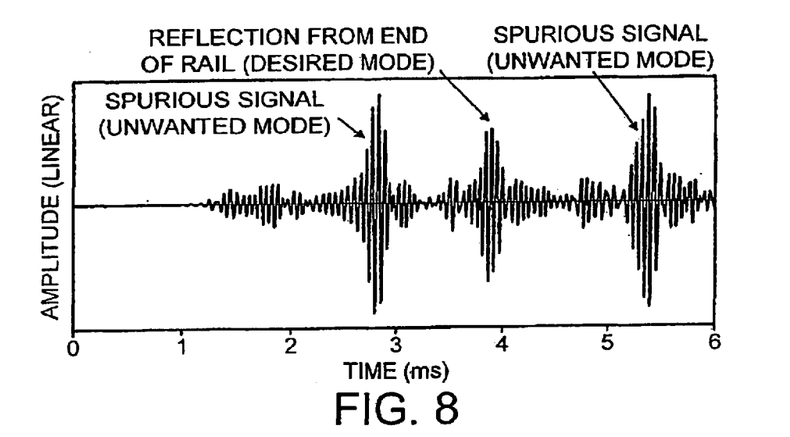
FIG. 8 is a linear plot of amplitude against time showing experimental results for propagation modes detected as a result of exciting guided waves in the rail using a single wave exciter.

FIG. 8 is a linear plot of amplitude against time in milliseconds corresponding to guided wave signals induced by a single wave exciter and detected by a single wave receiver. The signal comprises two large amplitude signals corresponding to unwanted excitation-modes and a signal of smaller amplitude corresponding to a reflection from the end of rail. The smaller amplitude signal corresponds to a desired mode.

Figure 9:
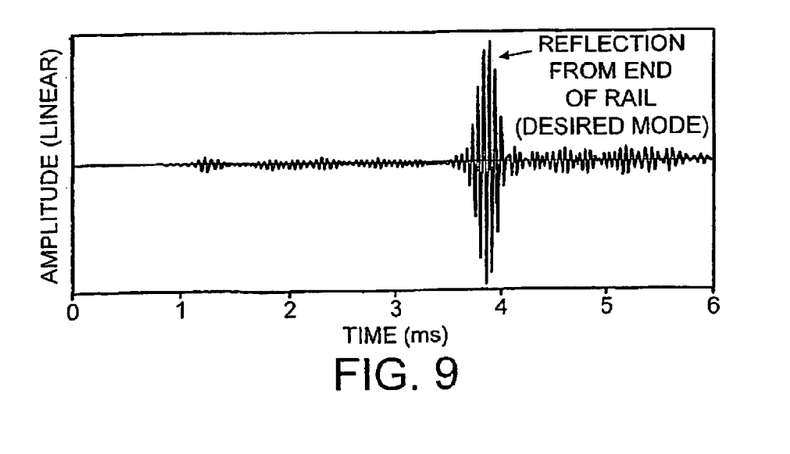
FIG. 9 is a linear plot of amplitude against time showing experimental results for propagation modes detected as a result of exciting guided waves in the rail using multiple wave exciters with independent driving voltages.

FIG. 9 is a linear plot of amplitude against time is milliseconds corresponding to guided wave signals induced using an array of transducers with weighted driving signals and detected using a pulse-echo mode of operation and synthetic aperture techniques. The same weightings were used in transmission and reception. In this case the amplitude of the desired mode reflected from the end of the rail is significantly larger than disturbances due to any unwanted modes.

The advantage of using an array of transducers rather than a single transducer is demonstrated by comparing the signal of FIG. 8, that is characterised by spurious modes of larger amplitude than the desired mode, with the signal of FIG. 9 where the spurious signals have amplitudes which are small relative to the amplitude of the desired mode. Thus using an array of transducers makes features such as defects and welds easy to identify.

Figure 10:
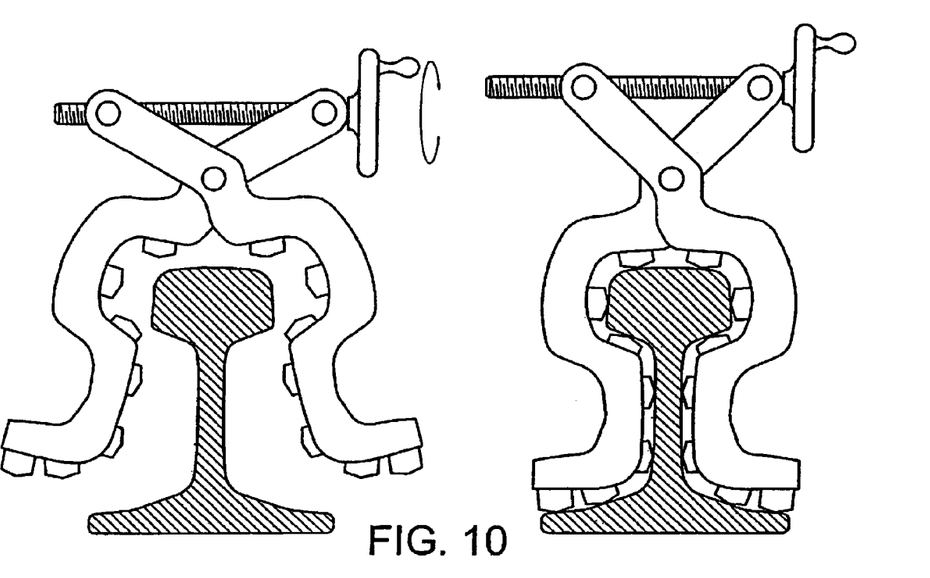
FIG. 10 illustrates a clamping mechanism according to a second embodiment of the invention used for operable attachment of an array of wave exciters to a rail.

FIG. 10 shows an array of transducers according to an embodiment of the invention. In this case the transducers are securely attached to a section of rail using a clamping mechanism. The clamping mechanism of this embodiment comprises two arms pivotally attached to each other close to half way along their length. Beyond the pivot, the arms cross over and are attached to a screw mechanism comprising a screw and a rotatable handle. The clamp has an open position and a closed position. The clamp is engaged by rotating the handle of the screw mechanism such that the pivoted arms are drawn together. The clamp is closed such that the transducers are operatively engaged on the surface of the rail in the positions shown. There are many possible alternative clamping mechanisms and it is also possible to permanently attach the transducers to the rail.

If the testing system is to be deployed while the rail is still in use by trains it will not be possible to deploy any transducers on the upper surface of the rail head. Although this makes mode control by weighting inputs to the transducer array more difficult, it is still possible to suppress undesired modes without using transducers to apply force over the upper surface of the rail head. The wave exciter array need not apply force at points distributed across the whole of the rail surface.

Figure 11:
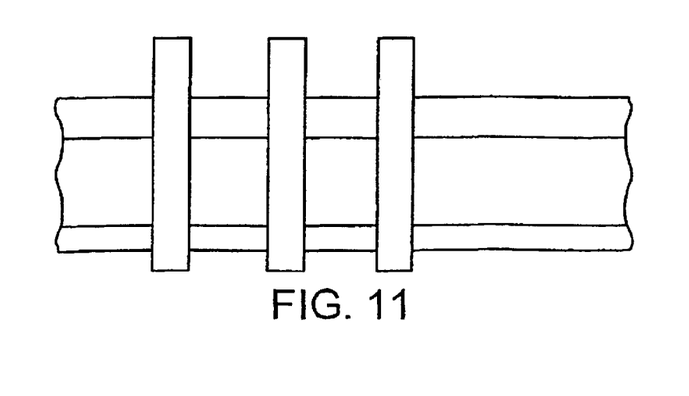
FIG. 11 schematically illustrates a plurality of transducer arrays spaced along the rail.

The mode control achievable using a single array of transducers with independent driving frequencies can be improved by using two or more wave exciter arrays separated by predetermined distances along the length of the rail (as illustrated in FIG. 11). Multiple exciter arrays can be used both to suppress unwanted excitations and to increase the amplitude of desired symmetric modes. Multiple arrays can be used to excite particular guided acoustic waves in a single direction along the rail. The use of more than one array is particularly suitable in the case where the transducers cannot be operably engaged on the upper surface of the rail head.

Because the wavelengths of alternative modes propagating at a given frequency are typically different it is possible to apply forces to the rail surface via at least two exciter arrays such that certain modes are reinforced while other modes are suppressed. Consider, for example, that the wavelength of a desired mode is $\lambda$ and the wavelength of an undesired mode is $2\lambda$. If two exciter arrays are placed a distance $\lambda$ apart along the length of the rail, and if an identical excitation signal is applied to both arrays, then the excitation will effectively be applied at points of equal phase on the desired mode but at points of opposite phase on the undesired mode. Thus the desired mode signal will be reinforced, however the undesired mode will be suppressed. In situations where the wavelengths of the desired and undesired modes are not simple multiples of each other, the enhancement of desired modes and suppression of undesired modes can be achieved by suitably adjusting the phases of the excitation signals in respective exciter arrays. The selectivity of guided wave modes propagating in the rail can be improved by employing more than the minimum number of exciter arrays that is required for the mode selection and direction of propagation selection.

The wave exciter arrays can be operated in pulse-echo mode such that each array acts as both an exciter and a receiver of reflected waves. When acting as receivers, the transducers of the array convert the mechanical displacements in the surface of the rail detected by each transducer to electrical signals. The electrical signals arising from the displacements detected at each transducer can be independently amplified according to a predetermined set of weightings. By appropriately adjusting the set of amplification weightings and summing the resulting electrical signals, a signal proportional to the amplitude of any propagating mode of interest may be obtained. The receiver weightings could be adjusted to obtain a signal proportional to the transmitted and reflected mode or to an anti-symmetric mode-converted reflection. In an alternative embodiment the displacements detected at each transducer can be amplified by the same amount and a weighted sum of the resultant signals is performed in computer software. This test is repeated for each transmitted mode received mode combination. A first test to detect the presence of any anti-symmetric reflected wave and a second test to detect reflections of the initially transmitted mode will typically be performed to obtain an indication of the geometry of a feature of the rail such as a weld or a defect. The reception of a pure guided wave mode, which is achievable by perfoming the weighted sum of the transducer displacements as described above, is just as important as the selective excitation of a pure guided wave mode to the effectiveness of the defect detection technique.

According to a further example embodiment, many transmitted mode-received mode combinations can be analysed simultaneously. In this case each transducer of the exciter array is used in turn to force excitations in the rail and the resulting reflections are received at each element of the receiving array, i.e. transmission using single transducer and reception using all transducers of the array. If separate transmitting and receiving transducers are used, sending is on one element of the transmitter array with receiving on all elements of the receiver array. If pulse-echo is used with the same transducers, receiving is on all elements including the transmitter (it is also possible to get reasonable (though somewhat degraded) performance by using a single array without pulse-echo—in this case sending is on one and receiving is on all the others. The first mentioned technique is similar to synthetic aperture techniques often used in ultrasonics. A synthetic aperture is a process in which different signals are measured and recorded one after the other and subsequently combined. Synthetic aperture focusing typically considers a single propagating mode and uses the combined measurements to inspect a particular region in space. In the case of the present invention the displacement amplitude as a function of time is measured at different positions of the transmitting and receiving transducers and a software addition process is used to isolate the behaviour of particular transmitted mode-received mode pairs. The advantage of this embodiment is that multiple pairs can be analysed using a single test. Although this process can result in the requirement to process a large volume of data for a given test, it is possible to reduce the number of excitations required by driving combinations of elements simultaneously rather than individually in a sequence. For example, if it is known that it is only necessary to examine transmitted mode—received mode combinations in which the transmitted mode is symmetric then an excitation can be applied simultaneously to two transducers of the exciter array that are symmetrically arranged with respect to the plane of symmetry. Two sets of processing will typically be required in the synthetic aperture configuration: a first set to detect the received mode corresponding to the symmetric excitation mode and a second set to detect the received mode corresponding to a non-symmetric mode to which the excited wave mode-converts.

What is claimed is:

1. Apparatus for inspecting a non axi-symmetric elongate body comprising:

at least one exciter array having a plurality of wave exciters operable to couple to an exterior surface of said elongate body;

a driver unit operable to generate driving signals to excite said plurality of wave exciters wherein each driving signal to a respective wave exciter of said array is weighted with respect to driving signals to other wave exciters in said array such that at least one guided acoustic wave mode is excited;

a receiving unit having a plurality of wave receivers capable of receiving reflected guided acoustic waves; and an analysis unit operable to analyze received waves to assess a condition of said non axi-symmetric elongate body.

2. Apparatus according to claim 1, comprising at least two exciter arrays located at predetermined distances with respect to each other along said elongate body wherein said exciter arrays are operable in co-operation to suppress the propagation of unwanted guided wave modes.

3. Apparatus according to claim 1, wherein at least one of said at least one exciter arrays is operable in a pulse-echo mode whereby said wave exciters also serve as wave receivers to excite a single guided wave mode and to receive a predetermined mode in a reflected wave.

4. Apparatus according to claim 1, wherein said analysis unit is operative to perform a weighted sum of received signals from each wave receiver to obtain a signal indicative of an amplitude of said predetermined mode of said reflected wave.

5. Apparatus according to claim 4, wherein said selected guided acoustic wave mode is a symmetric with respect to a plane of symmetry of said elongate body and said particular received wave mode is a non-symmetric mode arising from mode conversion of said excited mode.

6. Apparatus according to claim 5, wherein a received symmetric mode wave is also analysed by said analysis unit.

7. Apparatus according to claim 1, wherein said at least one exciter array is operable to sequentially excite a plurality of selected guided acoustic wave modes such that each excited mode assesses a different region of said non axisymmetric elongate body.

8. Apparatus according to claim 1, wherein said at least one exciter array is operable to excite a single guided acoustic wave mode that is symmetric with respect to a plane of symmetry of said elongate body and said analysis unit is operable to identify a defect in said elongate body by detecting in the received waves at least one of a non-symmetric mode and a symmetric mode.

9. Apparatus according to claim 8, wherein said analysis unit is operable to identify a defect in said elongate body by detecting one non-symmetric mode in the reflected waves.

10. Apparatus according to claim 1, wherein said at least one exciter array is secured to said exterior surface of said elongate body by a clamping mechanism.

11. Apparatus according to claim 1, wherein said at least one exciter array is permanently secured to said exterior surface of said elongate body by a bonding mechanism.

12. Apparatus according to claim 1, wherein said at least one exciter array comprises one of a plurality of electromagnetic acoustic transducers mounted on a moving train; and a plurality of electromagnetic acoustic transducers fixed to said elongate body.

13. Apparatus according to claim 1, wherein said wave exciters are transducer comprising a piezoelectric element that is polarised to deform when a voltage is applied across faces of said piezoelectric element.

14. Apparatus according to claim 1, wherein said elongate body is a railway rail.

15. Apparatus according to claim 1, wherein said plurality of exciters are sequentially driven.

16. Apparatus according to claim 15, wherein said analysis unit uses synthetic aperture processing to analyse received waves.

17. Apparatus according to claim 1 wherein said exterior surface to which said wave exciters couple is around a transverse cross-section of said elongate body.

18. A method of inspecting a non-axi-symmetric elongate body comprising the steps of:
   driving a plurality of wave exciters coupled to said elongate body with driver signals, each driver signal to a respective wave exciter being weighted with respect to driving signals to other wave exciters such that at least one guided acoustic wave mode is excited;
   receiving reflected guided acoustic waves; and
   analysing said received waves to assess a condition of said elongate body.

* * * * *